United States Patent [19]

Rohde et al.

[11] Patent Number: 4,987,146

[45] Date of Patent: Jan. 22, 1991

[54] N-HETARYL IMIDAZOLE DERIVATIVES

[75] Inventors: Ralph Rohde; Helmut Biere; Ralph Schmiechen; John S. Andrews; David N. Stephens, all of Berlin, Fed. Rep. of Germany

[73] Assignee: Schering Aktiengesellschaft, Berlin and Bergkamen, Fed. Rep. of Germany

[21] Appl. No.: 379,844

[22] Filed: Jul. 14, 1989

[30] Foreign Application Priority Data

Jul. 15, 1988 [DE] Fed. Rep. of Germany ....... 3824658

[51] Int. Cl.$^5$ ................... A61K 31/415; A61K 31/42;
A61K 31/425; A61K 31/44; A61K 31/445;
A61K 31/50; A61K 31/505; A61K 31/53;
A61K 31/535; A61K 31/54; C07D 401/04;
C07D 401/14; C07D 403/04; C07D 403/14;
C07D 405/04; C07D 405/14; C07D 409/04;
C07D 409/14; C07D 413/04; C07D 413/14

[52] U.S. Cl. ................................ 514/397; 514/227.8;
514/228.2; 514/233.5; 514/233.8; 514/234.5;
514/235.2; 514/231.5; 514/235.8; 514/236.2;
514/236.8; 514/236.5; 514/235.5; 514/242;
514/245; 514/252; 514/256; 514/269; 514/272;
514/273; 514/274; 514/275; 514/317; 514/318;
514/320; 514/321; 514/323; 514/324; 514/326;
514/333; 514/336; 514/337; 514/338; 514/339;
514/340; 514/341; 514/342; 514/343; 514/359;
514/362; 514/363; 514/364; 514/365; 514/367;
514/369; 514/370; 514/371; 514/372; 514/373;
514/374; 514/376; 514/377; 514/378; 514/380;
514/383; 514/384; 514/385; 514/394; 514/395;
548/131; 548/336; 548/235; 548/236; 548/233;
548/234; 548/229; 548/230; 548/232; 548/225;
548/226; 548/227; 548/228; 548/215; 548/240;
548/243; 548/244; 548/245; 548/246; 548/247;
548/248; 548/182; 548/183; 548/184; 548/185;
548/186; 548/187; 548/188; 548/189; 548/190;
548/191; 548/192; 548/193; 548/194; 548/195;
548/196; 548/198; 548/214; 548/137; 548/255;
548/161; 548/163; 548/164; 548/165; 548/169;
548/170; 548/171; 548/172; 548/173; 548/178;
548/179; 548/180; 548/327; 548/264.8;
546/269; 546/270; 546/271; 546/273; 546/274;
546/275; 546/276; 546/277; 546/278; 546/279;
546/193; 546/211; 546/210; 546/209; 546/208;
546/207; 546/199; 546/198; 546/201; 546/202;
546/196; 544/295; 544/320; 544/324; 544/328;
544/331; 544/405; 544/238; 544/357; 544/182;
544/194; 544/198; 544/207; 544/209; 544/212;
544/112; 544/113; 544/120; 544/122; 544/123;
544/124; 544/129; 544/130; 544/131; 544/132;
544/133; 544/134; 544/135; 544/137; 544/139;
544/138; 544/370; 544/360; 544/364; 544/367;
544/368; 544/369; 544/58.5; 544/58.6;
544/58.7; 544/60; 544/62; 548/264.8

[58] Field of Search ............... 514/397; 548/336, 137,
548/131, 235, 236, 233, 234, 229, 230, 232, 225,
226, 227, 228, 215, 240, 243, 244, 245, 246, 247,
248, 182, 183, 184, 185, 186, 187, 188, 189, 190,
191, 192, 193, 194, 195, 196, 198, 214, 137, 255,
262, 263, 264, 265, 266, 267, 268, 269, 161, 163,
164, 165, 169, 170, 171, 172, 173, 178, 179, 180,
327

[56] References Cited

U.S. PATENT DOCUMENTS 4,853,400 8/1989 Parsons et al. ...................... 548/336
4,866,183 9/1989 Kempe et al. ...................... 548/336
4,898,607 2/1990 Szczepanski ...................... 548/336

*Primary Examiner*—John M. Ford
*Attorney, Agent, or Firm*—Millen, White & Zelano

[57] ABSTRACT

N-hetaryl imidazole derivatives of general Formula I

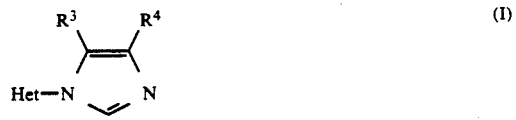

are disclosed in which

Het represents an optionally substituted monocyclic or bicyclic heteroaromate, $R^3$ represents hydrogen, a straight or branched $C_{1-6}$-alkyl group, or a $C_{1-6}$-alkoxy-alkyl group, and $R^4$ represents —COOR$^5$, —CONR$^6$R$^7$, —CN,

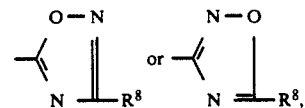

with $R^5$ meaning hydrogen, a straight or branched $C_{1-6}$-alkyl group, $R^6$ and $R^7$ are the same of different and represent hydrogen or a straight, branched, or cyclic alkyl group with up to 7 carbon atoms or, together with the nitrogen atom, form a saturated five or six ring optionally containing another heteroatom and $R^8$ means hydrogen or a straight, branched or cyclic alkyl group with up to 7 carbon atoms.

11 Claims, No Drawings

N-HETARYL IMIDAZOLE DERIVATIVES

SUMMARY OF THE INVENTION

The invention relates to new ZN-active (e.g., central nervous system affecting) imidazole derivatives of general Formula I

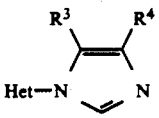
(I)

in which
Het represents a monocyclic or bicyclic optionally substituted heteroaromate,
$R^3$ represents hydrogen, a straight or branched $C_{1-6}$ alkyl group or a $C_{1-6}$ alkoxy alkyl group, and
$R^4$ represents —$COOR^5$, —$CONR^6R^7$, —CN,

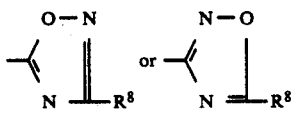

with $R^5$ meaning hydrogen, a straight or branched $C_{1-6}$ alkyl group, $R^6$ and $R^7$ are the same or different and represent hydrogen or a straight, branched, or cyclic alkyl group with up to 7 carbon atoms or, together with the nitrogen atom, form a saturated five- or six-membered ring optionally containing another heteroatom, and $R^8$ means hydrogen or a straight, branched, or cyclic alkyl group with up to 7 carbon atoms. Preferably,
Het is a mono- or bicyclic $C_{5-10}$-aromatic ring wherein 1-3 carbon atoms are replaced by at least one of sulfur, oxygen, or nitrogen; or such a ring substituted by one or two of halo, $C_{1-6}$-alkyl, $C_{1-6}$-alkenyl, $C_{1-6}$-alkynyl, $C_{3-6}$-cycloalkyl, $C_{1-4}$-alkoxy, $C_{1-6}$-alkylthioalkyl; nitro, cyano, thiocyanato, azido, $C_{1-5}$-alkanoyl, $C_{1-4}$-alkoxycarbonyl, carboxyl, sulfoxide, sulfonyl, sulfonylamino, amono, amido, or amino or amido substituted by at least one or two of $C_{1-4}$-alkyl, or $C_{2-5}$-alkanoyl,
$R^3$ is hydrogen, $C_{1-6}$-alkyl, or $C_{1-6}$-alkoxy-alkyl,
$R^4$ is —$COOR^5$, —$CONR^6R^7$, —CN,

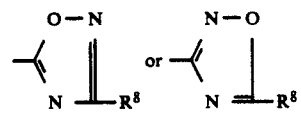

wherein
$R^5$ is hydrogen or $C_{1-6}$-alkyl, $R^6$ and $R^7$ are the same or different and are hydrogen, $C_{1-7}$-alkyl, $C_{3-7}$-cycloalkyl or, together with the nitrogen atom, form a saturated five- or six-membered ring optionally containing an oxygen, sulfur, or additional nitrogen atom, and $R^8$ is hydrogen, $C_{1-7}$-alkyl or $C_{3-7}$-cycloalkyl.

The monocyclic or bicyclic heteroaromate is preferably 5-10-membered and contains 1-3 heteroatoms such as sulfur, oxygen, and/or nitrogen. For example, the following heteroaromatic radicals can be mentioned: theinyl, furyl, pyrrolyl, pyranyl, imidazolyl, pyrazolyl, pyridyl, pyrimidinyl, pyrazinyl, pyridazinyl, oxazolyl, isoxazolyl, thiazolyl, isothiazolyl, thiadiazolyl, triazolyl, triazinyl, benzothiazolyl, benzimidazolyl, indolyl, benzofuranyl, benzothienyl.

5-6-Membered heteroaromates, which can contain 1-3 heteroatoms and optionally a fused benzene ring, are to be considered as preferred.

The heteroaromate can be substituted on any position with 1-2 substituents $R^1$ and, if a fused benzene ring is present, the latter is preferably substituted once or twice in the o-, m-, or p-position with a substituent $R^2$.

$R^1$ and $R^2$ can, respectively, mean halogen such as fluorine, chlorine, bromine and iodine, a straight-chain, branched, cyclic, saturated or unsaturated $C_{1-6}$ hydrocarbon radical, nitro, cyano, thiocyanate, azide, $C_{1-5}$ alkanoyl, $C_{1-4}$ alkoxycarbonyl, carboxyl, $C_{1-4}$-alkoxy, $C_{1-6}$-alkylthioalkyl, a sulfoxide, sulfonyl or sulfonylamino radical, or an amino or amide group optionally monosubstituted or disubstituted with $C_{1-4}$ alkyl or $C_{2-5}$ acyl, e.g., alkanoyl.

The following radicals are to be considered as preferred where Het is substituted: halogen, straight-chain or branched $C_{1-6}$ alkyl, $C_{1-4}$ alkoxy, nitro or optionally substituted amine.

In each case lower alkyl radicals such as methyl, ethyl, propyl, i-propyl, butyl, sec-butyl, isobutyl, tert-butyl as well as pentyl, hexyl, 2-methylbutyl, 2,2-dimethylpropyl are referred to as saturated, straight-chain or branched alkyl radicals.

As unsaturated alkyl groups the following alkenyl and alkinyl radicals can be mentioned as preferred: 1-propenyl, 2-propenyl, 3-methyl-2-propenyl, 2-propinyl. As cycloalkyls there can be mentioned, for example, cyclopropyl, cyclobutyl, cyclopentyl, cyclohexyl and cycloheptyl.

$R^6$, $R^7$ together with the nitrogen atom may form a saturated heterocyclic five- or six-membered ring optionally containing another heteroatom, thus this ring represents, for example, pyrrolidine, piperidine, morpholine, piperazine or thiomorpholine and optionally can be substituted with one to two $C_{1-4}$ alkyl groups such as, for example, 2,6-dimethylmorpholine or N-methylpiperazine.

$C_{1-4}$ alkoxy-$C_{1-2}$ alkyl, especially $C_{1-4}$ alkoxy-methyl are to be considered as preferred embodiments where $R^3$ is alkoxyalkyl, and straight or branched alkyl groups with 1-4 carbon atoms are to be considered as preferred embodiments where $R^3$ is alkyl. $COOR^5$ and

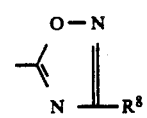

in which $R^5$ and $R^8$ are alkyl radicals and $R^8$ is a cycloalkyl radical, especially with up to 4 carbon atoms, are to be considered as preferred embodiments for $R^4$.

Because of their biological effectiveness as psychopharmaceutical agents the compounds according to the invention are suitable for administration to mammals, e.g., humans. Since the new compounds have a very good anxiolytic effectiveness and neither sedating or muscle-relaxing side effects occur, they can be used especially as anxiolytic agents, analogously to Diazepam to treat, e.g., anxiety. They can be formulated as psychopharmaceutical preparations, for example, for oral and parenteral use.

Physiologically compatible organic and inorganic vehicles, which are inert toward the compounds according to the invention, are suitable as formulation auxiliary agents.

As vehicles there can mentioned, for example, water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid ester, hydroxymethylcellolse and polyvinylpyrrolidone.

The pharmaceutical preparations can be sterilized and/or mixed with auxiliary agents, such as lubricants, preservatives, stabilizers, wetting agents, emulsifiers, buffering agents and dyes.

Especially injectable solutions or suspensions, especially aqueous solutions of active compounds in polyhydroxyethoxylated castor oil, are suitable for parenteral use. Surfactant auxiliary agents such as bile acid salts or animal or vegetable phospholipids, their mixtures as well as liposomes or their constituents can be used as vehicle systems.

Tablets, dragees or capsules with talc and/or a hydrocarbon vehicle or binding agent such as, for example, lactose, corn or potato starch are especially suitable for oral application. The application can also take place in liquid form such as, for example, as juice to which optionally a sweetener is added.

The compounds according to the invention are introduced in a dosage unit of 0.05 to 10 mg of active substance in a physiologically compatible vehicle.

The compounds according to the invention are applied in a dose of 0.1 to 300 mg/day, preferably 1–30 mg/day.

The production of the compounds according to the invention of formula I take place in that (a) an amine of general formula II

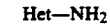

Het—NH$_2$                   (II), in which
Het has the meaning indicated in formula I,
is reacted with a 2-azadiene of general formula III

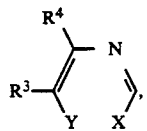

(III)

in which
R$^3$ and R$^4$ have the meaning indicated in formula I and X and Y represent leaving groups,
in the presence of acids at temperatures from 0° to 150° C. or (b) an imidazole derivative of general formula IV

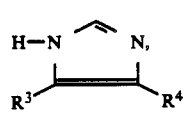

(IV)

in which R$^3$ and R$^4$ have the above-named meaning, is N-arylated with a heteroaromate of general formula Het-Z, in which Z represents a leaving group, and optionally the resulting isomers are separated, and then optionally in the compounds obtained according to (a) or (b) an ester group present in the molecule is transesterified or saponified, a free carboxyl group is optionally esterified, amidated or reacted with an amidoxime of the formula R$^8$—C(=NOH)NH$_2$ to the 5-oxadiazolyl derivative and optionally a nitrile group present in the molecule is hydrolyzed to the carbonyl amide or carboxyl group or converted by the imino group into the ester group (COOR$^5$) or with hydroxylamine by the amidoxime and then with an alkane carboxylic acid of the formula R$^8$—COOH or an activated derivative of the acid is converted into the 3-oxadiazolyl derivative and optionally a nitro group is reduced to the amino group and the latter then is optionally alkylated, acylated or sulfonylated or by a diazotization is exchanged for halogen, azide, cyano or thiocyanate.

The reaction according to the invention of amines of formula II with 2-azadienes of formula III to the imidazole derivatives of formula I takes place in the presence of acids at temperatures of 0° to 150° C. Leaving groups X and Y can be the same or different; C$_{1-3}$ dialkylamines such as dimethyl, diethyl and dipropyl amine, and cyclic amines, such as pyrrolidine are especially suited.

The reaction is performed, for example, so that the amine derivative and the azadiene in an organic acid, such as, for example, formic acid, acetic acid, propionic acid or trifluoroacetic acid is first stirred at room temperature and then heated to the boiling temperature of the reaction mixture (to about 120° C.).

The acid can be used at the same time as reagent and solvent. But solvents, such as, for example, alcohols, ethers, ketones, esters, such as ethyl acetate, hydrocarbons, such as, toluene, or halogenated hydrocarbons such as carbon tetrachloride can also be added.

The amount of acid can vary within broad limits, but is used in excess. Preferably, a 3–10-fold acid excess, relative to the amine and azadiene, is selected.

The molar ratio of amine and azadiene are not critical for the success of the reaction. Generally approximately equal molar amounts of the reactants will be used, and amount ratios of 1 mol of amine and 1–3 mol of azadiene are preferred. The reaction according to the invention basically can be performed in the above-indicated solvents with catalytic amounts of mineral acids such as sulfuric acid, hydrochloric acid, perchloric acid or organic acids such as p-toluenesulfonic acid and trifluoroacetic acid.

The advantage of the process according to the invention according to method (a) is in the chemoselective synthesis of imidazole derivatives with formation of only one isomer in a single process step.

The N-arylation of the imidazole derivatives of general formula IV can take place, for example, according to the method described by N. W. Gilman et al. J. Heterocycl. Chem. 14, 1157 (1977). Halogens, especially fluorine and iodine, are suitable as leaving groups Z. Arylation according to method (b) is performed in the presence of bases such as alkali hydroxide, alkali hydride optionally in the presence of phase transfer catalysts, butyllithium or lithium diisopropylamide, preferably with alkali hydride.

Temperatures of −78° C. to 100° C., preferably 0° C. to 50° C., are suitable for the reaction. Aprotic polar solvents, for example, aliphatic and cyclic ethers such as diethyl ether, tetrahydrofuran, i.a., and dimethylformamide are suitable as solvents for the arylation.

All usual methods are suitable for the optionally subsequent transesterification. There can be mentioned, for example, the reaction of carboxylic acid ester with the corresponding alcohol in the presence of the alcoholate or with the corresponding alcohol with the titanium tetraalcoholate or with the alcohol in the presence of an acid. The transesterification is performed at temperatures of about 0° to 120° C.

The optionally subsequent saponification of the ester group suitably takes place in an alkaline manner, and the ester is refluxed in dilute aqueous or alcoholic alkali lye, such as potassium or sodium hydroxide.

The esterification of the carboxyl group takes place in a way known in the art with the corresponding alcohol in acid or in the presence of an activated acid derivative. Acid chloride, acid imidazolide or acid anhydride, for example, are suitable as activated acid derivatives.

For amidation the imidazole-4-carboxylic acid or the corresponding ester with the help of N,N'-carbonyldiimidazole or dicyclohexylcarbodiimide is reacted with a primary or secondary amine of the general formula

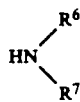

The reaction can also take place in a way known in the art by activated acid derivatives such as by the anhydride or the mixed anhydride with chloroformic acid ester. Usually the amidation is performed in an aprotic solvent such as dimethylformamide, tetrahydrofuran, toluene or methylene chloride at temperatures of about 0° to 100° C.

For introduction of the 5-oxadiazolyl radical, the imidazole-4-carboxylic acid with an amidoxime of formula $R^8$—C(=NOH)NH$_2$ has the meaning indicated in formula I, can be brought in an inert solvent at room temperature to the boiling temperature of the reaction mixture for condensation. Toluene and dimethylformamide are suitable as inert solvents. Advantageously the free carboxylic acid is suitably activated before the condensation reaction. For this purpose, the free acid can be converted into the mixed anhydride, the activated ester or the chloride. An activation with imidazole/thionylchloride in an aprotic solvent such as dioxane, tetrahydrofuran, dimethylformamide or N-methylpyrrolidone at temperatures between 0° and 50° C. has proved successful.

The optionally subsequent modification of the nitrile group can be performed according to known methods. For example, the nitrile group can be connected by acid or alkaline hydrolysis into the carbonylamide or carboxyl group or with the corresponding alcohol with addition of hydrochloric-acid gas by the imino ester group into the ester group.

For the introduction of the 3-oxadiazolyl radical the imidazole-4-carbonitrile is reacted in a way known in the art with hydroxylamine to amidoxime and then is condensed with an alkane carboxylic acid of formula $R^8$—COOH, in which $R^8$ has the meaning indicated in formula I, or an activated derivative of the acid in an inert solvent. The condensation is performed in a way similar as in the case of the 5-oxadiazolyl compound.

The reduction of the nitro group to the amino group can take place, for example, catalytically, by hydrogenation being performed under normal pressure or H$_2$ pressure in polar solvents at room temperature. Palladium on a support such as carbon or platinum in finely divided form can be used as catalyst; in compounds with halogen, preferably Raney nickel is used as catalyst. Suitable polar solvents for the reduction are, for example, alcohols or ethers such as methanol, ethanol, diethyl ether, tetrahydrofuran or their mixtures.

The introduction of the cyano group can take place with the help of the Sandmeyer reaction; for example, the diazonium salts intermediately formed from the amino compounds with nitrites can be reacted with alkali cyanides in the presence of Cu(I) cyanide.

The introduction of the halogens chlorine, bromine or iodine can take place, for example, by the amino groups also according to the Sandmeyer reaction, by the diazonium salts, intermediately formed with nitrites, being reacted with Cu(I) chloride or Cu(I) bromide in the presence of the corresponding acid, hydrochloric acid or hydrobromic acid or with potassium iodide.

Introduction of fluorine can take place, for example, by Balz Schiemann reaction of the diazonium tetrafluoroborate.

Introduction of the azido or thiocyanate group can also take place by Sandmeyer reaction of the diazonium salt with alkali azide or alkali thiocyanate.

If an alkylation, acylation or sulfonylation of the amino group is desired, it can be alkylated, acylated or sulfonylated, for example, with alkyl, acyl or sulfonyl halides according to the usual methods.

STARTING MATERIALS

The amino heterocycles of general Formula II and the azadienes of general Formula III used as starting materials are mainly known or can be produced according to known methods.

The 2-azadienes are described for example, in Liebigs Ann. Chem. 1980, 334, DE-OS No. 29 19 891 and in Liebigs Ann. Chem. 1986, 1749.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding West German Application No. P 38 24 658.9, filed July 15, 1988, are hereby incorporated by reference.

EXAMPLES

Production of the 2-azadienes used in the examples is described by the following examples.

Azadiene 1

1,4-Bis(dimethylamino)-2-aza-1,3-butadiene-3-carboxylic acid ester

The synthesis takes place according to Liebigs Ann. Chem. 1980, 344.

Azadiene 2

1,4-Bis(dimethylamino)-3-(3-ethyl-1,2,4-oxadiazol-5-yl)-2-aza-1,3-butadiene

The synthesis takes place according to Liebigs Ann. Chem. 1986, 1749.

Azadiene 3

(a)
3-Ethyl-5-(N-dimethylaminomethyleneaminomethyl)-1,2,4-oxadiazole

A mixture of 26 g of 5-aminomethyl-3-ethyl-1,2,4-oxadiazole and 30 ml of dimethylformamide dimethylacetal is heated for 6½ hours to 80° C. (bath temperature). Then 16 ml of methanol is distilled off and the formed product is purified by bulb tube distillation. 27.9 g (74.8%) of oil with a boiling point of 130°-150° C. (0.05 torr); $n_D^{20}$: 1.4924.

(b)
1-dimethylamino-3-(3-ethyl-1,2,4-oxadiazol-5-yl)-4-(1-pyrrolidinyl)-2-azapenta-1,3-diene (E,Z mixture)

13.6 g of the product obtained under a, 15.0 g of dimethylacetamide dimethylacetal and 8.0 g of pyrrolidine are heated for 21 hours under nitrogen to 80° C. (bath temperature). Then the formed alcohol is distilled off and the reaction product is purified by bulb tube distillation. 15.4 g of a fraction is obtained which distills at 215°-230° C. (0.04 torr). By recrystallization from n-hexane, 9.5 g (45.7%) of azadiene 5 with a melting point of 59°-62° C. is recovered.

Azadiene 4

(a) Methoxyacetic acid dimethylamide dimethylacetal 42.2 g of methoxyacetic acid dimethylamide is added in three portions to 53.4 g of trimethyloxonium tetrafluoroborate with cooling. Then the reaction mixture is stirred for 2 hours at room temperature and then allowed to stand overnight. After dissolving in 40 ml of dichloromethane the formed salt is slowly added to a solution of sodium methoxide in methanol (produced by dissolving of 10.4 g of sodium in 225 ml of methanol). Then it is stirred for 2 hours more at room temperature. For working up, the formed precipitate is suctioned off and washed with a little ethanol. After distilling off of the solvent, the filtrate forms 2 phases. 21.8 g (36%) of the desired product with a boiling point of 54°-57° C. (14 torr); $n_D^{20}$: 1.4204, is obtained from the upper phase by bulb tube distillation.

(b)
1-Dimethylamino-3-(3-ethyl-1,2,4-oxadiazol-5-yl)-5-methoxy-4-(1-pyrrolidinyl)-2-azapenta-1,3-diene (E,Z mixture)

8.8 g of the product produced under a is reacted with 6.6 g of 3-ethyl-5-(N-dimethylaminomethyleneaminomethyl)-1,2,4-oxadiazol and 4.5 ml of pyrrolidine similarly to the production of azadiene 3. 11.8 g (quant.) of azadiene 6 with a boiling point of 200°-240° C. (0.05 torr) is obtained by bulb tube distillation.

EXAMPLE 1

(a) 1-(2-Thiazolyl)-imidazole-4-carboxylic acid ethyl ester

A solution of 1.94 g of azadiene 1 in 7 ml of glacial acetic acid is mixed with 700 mg of 2-aminothiazole with cooling and then is stirred for 16 hours at room temperature under nitrogen. Then it is heated for 3 hours to 100° C. (bath temperature). For working up, the reaction mixture is mixed with potassium carbonate solution with cooling, the formed crystallizate is suctioned off, washed again with water and dried. By recrystallization from ethyl acetate, 986 mg (63%) of the title compound with a melting point of 142°-143° C. is obtained.

Analogously to example 1(a) there are obtained:

(b)
4-(3-Ethyl-1,2,4-oxadiazol-5-yl)-1-(2-thiazolyl)-imidazole by reaction of azadiene 2 with 2-aminothiazole; melting point 147°-148° C. (ethanol).

(c) 1-(5-Methyl-3-isoxazolyl)-imidazole-4-carboxylic acid ethyl ester by reaction of azadiene 1 with 3-amino-5-methyl-isoxazole; melting point 142°-143° C. (ethanol).

(d)
1-(5-Methyl-1,3,4-thiadiazol-2-yl)-imidazole-4-carboxylic acid ethyl ester by reaction of azadiene 1 with 2-amino-5-methyl-1,3,4-thiadiazole; melting point 121°-122° C. (ethanol).

(e) 1-(1H-1,2,4-triazol-3-yl)-imidazole-4-carboxylic acid ethyl ester by reaction of azadiene 1 with 3-amino-1,2,4-triazole; melting point 220°-222° C. (ethanol).

(f)
4-(3-Ethyl-1,2,4-oxadiazol-5-yl)-1-(1H-1,2,4-triazol-3-yl)-imidazole by reaction of azadiene 2 with 3-amino-1,2,4-triazole; melting point 242°-243° C. (ethanol).

EXAMPLE 2

(a) 1-(2-Benzothiazolyl)-imidazole-4-carboxylic acid ethyl ester 1.4 g of azadiene 1 is reacted with 751 mg of 2-aminobenzothiazole in 5 ml of glacial acetic acid in the way indicated under example 1(a). After working up and recrystallization from ethanol, 627 mg (45.9%) of the title compound with a melting point of 131°-133° C. is obtained.

Analogously to 2(a) there are obtained:

(b) 1-(2-Benzimidazolyl)-imidazole-4-carboxylic acid ethyl ester by reaction of azadiene 1 with 2-aminobenzimidazole; melting point 252°-253° C. (ethanol).

(c)
4-(3-Ethyl-1,2,4-oxadiazol-5-yl)-1-(3-indolyl)-imidazole by reaction of azadiene 2 with 3-aminoindole; melting point 198°-199° C. (acetonitrile).

EXAMPLE 3

(a) 1-(3-Pyridyl)-imidazole-4-carboxylic acid ethyl ester 5.6 g of azadiene 1 is reacted with 1.9 g of 3-aminopyridine in 20 ml of glacial acetic acid in the way described under example 1(a). After working up and recrystallization from toluene, 2.39 g (55%) of the title compound with a melting point of 102°–103° C. is obtained.

Analogously to example 3(a) there are obtained:

(b) 1-(2-Pyridyl)-imidazole-4-carboxylic acid ethyl ester by reaction of azadiene 1 with 2-aminopyridine; melting point 118°–119° C. (acetonitrile).

(c)
4-(3-Ethyl-1,2,4-oxadiazol-5-yl)-1-(2-pyridyl)-imidazole by reaction of azadiene 2 with 2-aminopyridine; melting point 162°–163° C. (ethanol).

(d)
4-(3-Ethyl-1,2,4-oxadiazol-5-yl)-1-(3-pyridyl)-imidazole by reaction of azadiene 2 with 3-amino-pyridine; melting point 152°–153° C. (ethanol).

(e)
4-(3-Ethyl-1,2,4-oxadiazol-5-yl)-5-methyl-1-(3-pyridyl)-imidazole by reaction of azadiene 3 with 3-aminopyridine; melting point 127°–128° C. (ethanol).

(f)
4-(3-Ethyl-1,2,4-oxadiazol-5-yl)-5-methoxymethyl-1-(3-pyridyl)-imidazole by reaction of azadiene 4 with 3-aminopyridine; melting point 70°–72° C. (diisopropyl ether).

EXAMPLE 4

1-(3-Pyridyl)-imidazole-4-carboxylic acid isopropyl ester

A solution of 500 mg of the compound produced under example 3(a) in 30 ml of anhydrous isopropanol is mixed with 0.34 ml of titanium isopropylate under nitrogen and refluxed for four hours. Then portions of 0.04 ml of titanium propylate each are added several times, until no starting material can be detected any longer on the thin-film chromatogram (hexane/acetone=1:1). For working up, the reaction mixture is concentrated by evaporation, the residue is taken up with ethyl acetate and shaken out with a little 2N HCl. Then it is neutralized with sodium bicarbonate solution and reextracted several times with ethyl acetate. The organic phase is washed with water, dried over sodium sulfate and concentrated by evaporation. 320 mg (60%) of the title compound with a melting point of 130°–131° C. (toluene) is obtained from the residue by chromatography on silica gel with hexane/acetone (6:4).

EXAMPLE 5

1-(3-Pyridyl)-imidazole-4-carboxylic acid 700 mg of the compound produced under example 4 is mixed with 1.6 ml of 2N NaOH and stirred for 5 minutes at room temperature. For working up, 1.6 ml of 2N HCl is added, the formed crystals are suctioned off, thoroughly rewashed with water and dried. In this way, 540 mg (89%) of the title compound with a melting point of 265°–266° C. (decom.) is obtained.

EXAMPLE 6

1-(3-Pyridyl)-imidazole-4-carboxylic acid-tert-butyl ester

A solution of 230 mg of the compound described under example 5 in 10 ml of anhydrous dimethylformamide is mixed with 2 ml of dimethylformamide-di-tert-butyl acetal under protective gas and refluxed for 2½ hours. For working up, the reaction mixture is concentrated by evaporation, the residue is suspended with toluene and filtered. After concentration of the filtrate by evaporation, 90 mg (30%) of the title compound with a melting point of 81°–82° C. (toluene) is obtained by chromatography of the raw product on silica gel with toluene/ethanol (95:5).

EXAMPLE 7

(a) 1-(5-Chloro-2-pyridyl)-imidazole-4-carboxylic acid ethyl ester 643 mg of 2-amino-5-chloropyridine is added to a solution of 1.4 g of azadiene 1 in 5 ml of glacial acetic acid with cooling. Then it is stirred for 16 hours under nitrogen at room temperature and 3 hours at 100° C. (bath temperature). For working up, the reaction mixture is poured on ice/water and made alkaline with potassium carbonate solution. The formed precipitate is suctioned off, rewashed thoroughly with water and dried. By recrystallization from ethanol, 658 mg (52%) of the title compound with a melting point of 163°–164° C. is obtained. Analogously to example 7(a) there are obtained:

(b)
1-(5-Chloro-2-pyridyl)-4-(3-ethyl-1,2,4-oxadiazol-5-yl)-imidazole by reaction of azadiene 2 with 2-amino-5-chloropyridine; melting point 224°–226° C. (ethanol).

(c) 1-(5-Nitro-2-pyridyl)-imidazole-4-carboxylic acid ethyl ester by reaction of azadiene 1 with 2-amino-5-nitropyridine; melting point 212°–214° C. (ethanol).

(d)
4-(3-Ethyl-1,2,4-oxadiazol-5-yl)-1-(5-nitro-2-pyridyl)-imidazole by reaction of azadiene 2 with 2-amino-5-nitropyridine; melting point 228°–229° C. (ethanol).

(e) 1-(3,5-Dichloro-2-pyridyl)-imidazole-4-carboxylic acid ethyl ester by reaction of azadiene with 2-amino-3,5-dichloropyridine; melting point 114°–115° C. (ethanol).

(f)
1-(3,5-Dichloro-2-pyridyl)-4-(3-ethyl-1,2,4-oxadiazol-5-yl)-imidazole by reaction of azadiene 2 with 2-amino-3,5-dichloropyridine; melting point 132°–133° C. (ethanol).

(g) 1-(2-Pyrazinyl)-imidazole-4-carboxylic acid ethyl ester by reaction of azadiene 1 with 2-aminopyrazine; melting point 128°–129° C. (isopropanol).

(h)
4-(3-Ethyl-1,2,4-oxadiazol-5-yl)-1-(2-pyrazinyl)-imidazole by reaction of azadiene 2 with 2-aminopyrazine; melting point 166°–167° C. (ethanol).

(i) 1-(1,2,4-Triazin-3-yl)-imidazole-4-carboxylic acid ethyl ester by reaction of azadiene 1 with 3-amino-1,2,4-triazine; melting point 193°-194° C. (ethanol).

(j) 4-(3-Ethyl-1,2,4-oxadiazol-5-yl)-1-(1,2,4-triazin-3-yl)-imidazole by reaction of azadiene 2 with 3-amino-1,2,4-triazine; melting point 181°-182° C. (ethanol).

(k) 4-(3-Ethyl-1,2,4-oxadiazol-5-yl)-1-(5-isopropoxy-2-pyrimidinyl)-imidazole by reaction of azadiene 2 with 2-amino-5-isopropoxypyrimidine; melting point 156°-157° C. (diisopropylether).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An N-hetaryl imidazole derivative of the formula

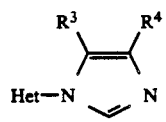

wherein
Het- is thienyl, furyl, pyrrolyl, pyranyl, imidazolyl, pyrazolyl, pyridyl, pyrimidinyl, pyrazinyl, pyridazinyl, oxazolyl, isoxazolyl, thiazolyl, isothiazolyl, thiadiazolyl, triazolyl, triazinyl, benzothiazolyl, benzimidazolyl, indolyl, benzofuranyl, benzothienyl; or one of the above substituted by one or two of halo, $C_{1-6}$-alkyl, $C_{1-4}$-alkoxy, nitro, amino, or amino substituted by one or two of $C_{1-4}$-alkyl or $C_{2-5}$-alkanoyl;
$R^3$ is hydrogen, $C_{1-6}$-alkyl, or $C_{1-6}$-alkoxy-alkyl,
$R^4$ is —COOR$^5$, —CONR$^6$R$^7$, —CN,

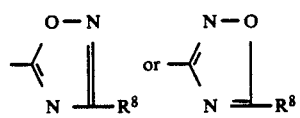

wherein
$R^5$ is hydrogen or $C_{1-6}$-alkyl, $R^6$ and $R^7$ are the same or different and are hydrogen, $C_{1-7}$-alkyl, $C_{1-7}$-cycloalkyl or, together with the nitrogen atom, are pyrrolidine, piperidine, morpholine, piperazine, or thiomorpholine, each optionally substituted with one or two $C_{1-4}$-alkyl groups and $R^8$ is hydrogen, $C_{1-7}$-alkyl or $C_{3-7}$-cycloalkyl.

2. A compound according to claim 1, wherein $R^3$ is $C_{1-4}$-alkyl or hydrogen.

3. A compound according to claim 2, wherein $R^3$ is $C_{1-4}$-alkoxy-methyl.

4. A compound according to claim 1, wherein $R^4$ is COOR$^5$ or

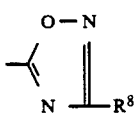

$R^5$ is $C_{1-6}$-alkyl, and $R^8$ is $C_{1-7}$-alkyl or $C_{3-7}$-cycloalkyl.

5. An imidazole derivative according to claim 1, wherein $R^4$ is COOR$^5$,

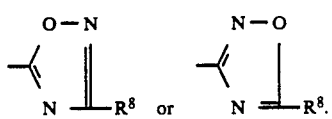

6. 1-(2-Thiazolyl)-imidazole-4-carboxylic acid ethyl ester,
4-(3-ethyl-1,2,4-oxadiazol-5-yl)-1-(2-thiazolyl)-imidazole,
1-(5-methyl-3-isoxazolyl)-imidazole-4-carboxylic acid ethyl ester,
1-(5-methyl-1,3,4-thiadiazol-2-yl)-imidazole-4-carboxylic acid ethyl ester,
1-(1H-1,2,4-triazol-3-yl)-imidazole-4-carboxylic acid ethyl ester,
4-(3-ethyl-1,2,4-oxadiazol-5-yl)-1-(1H-1,2,4-triazol-3-yl)-imidazole,
1-(2-benzothiazolyl)-imidazole-4-carboxylic acid ethyl ester,
1-(2-benzimidazolyl)-imidazole-4-carboxylic acid ethyl ester,
4-(3-ethyl-1,2,4-oxadiazol-5-yl)-1-(3-indolyl)-imidazole,
1-(3-pyridyl)-imidazole-4-carboxylic acid ethyl ester,
1-(2-pyridyl)-imidazole-4-carboxylic acid ethyl ester,
4-(3-ethyl-1,2,4-oxadiazol-5-yl)-1-(2-pyridyl)-imidazole,
4-(3-ethyl-1,2,4-oxadiazol-5-yl)-1-(3-pyridyl)-imidazole,
4-(3-ethyl-1,2,4-oxadiazol-5-yl)-5-methyl-1-(3-pyridyl)-imidazole,
4-(3-ethyl-1,2,4-oxadiazol-5-yl)-5-methoxymethyl-1-(3-pyridyl)-imidazole,
1-(3-pyridyl)-imidazole-4-carboxylic acid isopropyl ester,
1-(3-pyridyl)-imidazole-4-carboxylic acid,
1-(3-pyridyl)-imidazole-4-carboxylic acid tert-butyl ester,
1-(5-chloro-2-pyridyl)-imidazole-4-carboxylic acid ethyl ester,
1-(5-chloro-2-pyridyl)-4-(3-ethyl-1,2,4-oxadiazol-5-yl)-imidazole,
1-(5-nitro-2-pyridyl)-imidazole-4-carboxylic acid ethyl ester,
4-(3-ethyl-1,2,4-oxadiazol-5-yl)-1-(5-nitro-2-pyridyl)-imidazole,
1-(3,5-dichloro-2-pyridyl)-imidazole-4-carboxylic acid ethyl ester,
1-(3,5-dichloro-2-pyridyl)-4-(3-ethyl-1,2,4-oxadiazol-5-yl)-imidazole,
1-(2-pyrazinyl)-imidazole-4-carboxylic acid ethyl ester,
4-(3-ethyl-1,2,4-oxadiazol-5-yl)-1-(2-pyrazinyl)-imidazole,
1-(1,2,4-triazin-3-yl)-imidazole-4-carboxylic acid ethyl ester,
4-(3-ethyl-1,2,4-oxadiazol-5-yl)-1-(1,2,4-triazin-3-yl)-imidazole, 4-(3-ethyl-1,2,4-oxadiazol-5-yl)-1-(5-isopropoxy-2-pyrimidinyl-imidazole, each a compound of claim 1.

7. A pharmaceutical composition comprising an effective amount of a compound of claim 1 and a pharmaceutically acceptable carrier.

8. A pharmaceutical composition comprising an effective amount of a compound of claim 8 and a pharmaceutically acceptable carrier.

9. A pharmaceutical composition comprising an effective amount of a compound of claim 9 and a pharmaceutically acceptable carrier.

10. A method of achieving an anxiolytic effect in a host, comprising administering an effective amount of a compound of claim 1.

11. A method according to claim 10, wherein the effective amount is 0.1 to 300 mg/day.

* * * * *